United States Patent [19]

Fuisz

[11] Patent Number: 5,490,993
[45] Date of Patent: Feb. 13, 1996

[54] METHOD OF PREPARING A PROTEINACEOUS FOOD PRODUCT CONTAINING A MELT SPUN MATRIX AND PRODUCT THEREOF

[75] Inventor: Richard C. Fuisz, Great Falls, Va.

[73] Assignee: Fuisz Technologies Ltd., Chantilly, Va.

[21] Appl. No.: 410,333

[22] Filed: Mar. 24, 1995

Related U.S. Application Data

[62] Division of Ser. No. 289,926, Aug. 12, 1994, Pat. No. 5,431,950, which is a division of Ser. No. 163,120, Dec. 6, 1993, Pat. No. 5,374,447, which is a division of Ser. No. 80,479, Jun. 22, 1993, Pat. No. 5,286,513, which is a division of Ser. No. 851,650, Mar. 16, 1992, Pat. No. 5,236,734, which is a continuation-in-part of Ser. No. 602,485, Oct. 24, 1990, Pat. No. 5,096,492, which is a continuation-in-part of Ser. No. 169,838, Mar. 18, 1988, Pat. No. 4,855,326, which is a continuation-in-part of Ser. No. 40,371, Apr. 20, 1987, abandoned.

[51] Int. Cl.⁶ .......................... A23L 1/314; A23L 1/315; A23L 1/317

[52] U.S. Cl. .................... 426/92; 426/644; 426/646

[58] Field of Search ................ 426/89, 92, 641, 426/643, 644, 646, 652, 656, 657, 658, 417

[56] References Cited

U.S. PATENT DOCUMENTS

| | | |
|---|---|---|
| 2,826,169 | 3/1958 | Le Veen . |
| 2,918,404 | 12/1959 | Mende et al. . |
| 3,019,745 | 2/1962 | Du Bois et al. . |
| 3,036,532 | 5/1962 | Bowe . |
| 3,067,743 | 12/1962 | Merton et al. . |
| 3,070,045 | 12/1962 | Bowe . |
| 3,073,262 | 1/1963 | Bowe . |
| 3,095,258 | 6/1963 | Scott . |
| 3,131,428 | 5/1964 | Mika . |
| 3,308,221 | 3/1967 | Opfell . |
| 3,324,061 | 6/1967 | Tanquary et al. . |
| 3,482,998 | 10/1969 | Carroll et al. . |
| 3,557,717 | 1/1971 | Chivers . |
| 3,596,675 | 7/1971 | Ash et al. . |
| 3,615,671 | 10/1971 | Schoaf . |
| 3,625,214 | 12/1971 | Higuchi . |
| 3,676,148 | 7/1972 | De Wesse et al. . |
| 3,686,000 | 8/1972 | Lawrence . |
| 3,723,134 | 3/1973 | Chivers . |
| 3,762,846 | 10/1973 | Chivers . |
| 3,856,443 | 12/1974 | Salvi . |
| 3,856,846 | 10/1973 | Chivers . |
| 3,875,300 | 4/1975 | Homm et al. . |
| 3,925,525 | 12/1975 | LaNieve . |
| 3,930,043 | 12/1975 | Warning et al. . |
| 3,951,821 | 4/1976 | Davidson . |
| 3,967,623 | 7/1976 | Butterworth et al. . |
| 3,992,265 | 11/1976 | Hansen . |
| 4,090,920 | 5/1978 | Studer, Jr. . |
| 4,136,145 | 1/1979 | Fuchs et al. . |
| 4,153,512 | 5/1979 | Messner et al. . |
| 4,293,570 | 10/1981 | Vadasz . |
| 4,303,684 | 12/1981 | Pitchon et al. . |
| 4,348,420 | 9/1982 | Lynch et al. . |
| 4,371,516 | 2/1983 | Gregory et al. . |
| 4,376,743 | 3/1983 | Dees . |
| 4,492,685 | 1/1985 | Keith et al. . |
| 4,496,592 | 1/1985 | Kuwahara et al. . |
| 4,500,546 | 2/1989 | Turbak et al. . |
| 4,511,584 | 4/1985 | Percel et al. . |
| 4,526,525 | 7/1985 | Oiso et al. . |
| 4,585,797 | 4/1986 | Cioca . |
| 4,619,833 | 10/1986 | Anderson . |
| 4,772,477 | 9/1988 | Weiss et al. . |
| 4,793,782 | 12/1988 | Sullivan . |
| 4,855,326 | 8/1989 | Fuisz . |
| 4,873,085 | 10/1989 | Fuisz . |
| 4,978,537 | 12/1990 | Song . |
| 4,997,856 | 3/1991 | Fuisz . |
| 5,011,532 | 4/1991 | Fuisz . |
| 5,028,632 | 7/1991 | Fuisz . |
| 5,034,421 | 7/1991 | Fuisz . |
| 5,073,387 | 12/1991 | Whistler . |
| 5,082,682 | 1/1992 | Peterson . |
| 5,082,684 | 1/1992 | Fung . |
| 5,084,295 | 1/1992 | Whelan et al. . |
| 5,089,606 | 2/1992 | Cole et al. . |
| 5,094,872 | 3/1992 | Furcsik et al. . |
| 5,096,492 | 3/1992 | Fuisz . |
| 5,196,199 | 3/1993 | Fuisz . |
| 5,236,734 | 8/1993 | Fuisz . |
| 5,279,849 | 1/1994 | Fuisz . |

FOREIGN PATENT DOCUMENTS

| | | |
|---|---|---|
| 88/2771 | 4/1988 | South Africa . |
| 88/2770 | 4/1988 | South Africa . |
| 89/9318 | 12/1989 | South Africa . |
| 90/2139 | 3/1990 | South Africa . |
| 90/8406 | 10/1990 | South Africa . |
| 90/9092 | 11/1990 | South Africa . |

*Primary Examiner*—Arthur L. Corbin
*Attorney, Agent, or Firm*—Hoffmann & Baron

[57] ABSTRACT

Proteinaceous products such as hamburgers or soy-based materials are formed containing an oleaginous matrix, which is formed by melt-spinning an oleaginous substance with a carrier material, such as sucrose or water-soluble cellulosic materials. Methods of preparing such products are also disclosed.

4 Claims, No Drawings

METHOD OF PREPARING A PROTEINACEOUS FOOD PRODUCT CONTAINING A MELT SPUN MATRIX AND PRODUCT THEREOF

This application is a division of U.S. Ser. No. 289,926, Aug. 12, 1994, now U.S. Pat. No. 5,431,950, which is a division of U.S. Ser. No. 163,120, Dec. 6, 1993, now U.S. Pat. No. 5,374,447, which is a division of Ser. No. 080,479, Jun. 22, 1993, now U.S. Pat. No. 5,286,513 which is a division of Ser. No. 851,650, Mar. 16, 1992, now U.S. Pat. No. 5,236,734 which is a continuation-in-part of U.S. patent application Ser. No. 602,485, Oct. 24, 1990, (U.S. Pat. No. 5,096,492) which is a continuation-in-part of Ser. No. 169,838, Mar. 18, 1988, now U.S. Pat. No. 4,855,326 which, in turn, is a continuation-in-part of U.S. patent application Ser. No. 040,371, filed Apr. 20, 1987, now abandoned. The disclosure of the '326 patent is incorporated herein by reference.

BACKGROUND OF THE INVENTION

The present invention relates to new saccharide-based matrices containing oleaginous materials which can be used in food products. The invention also relates to methods of making and using the oleaginous matrix.

As an outgrowth of experimentation with a varied catalog of substances, it has been discovered that spinning a substance with sugar can alter the medium in which a particular substance can either dissolve or become dispersed, the latter while forming a colloid or colloidal-like dispersion. Whether or not the dispersions to be described herein represent true colloidal dispersions or only pseudo-colloidal dispersions, has yet to be determined. What is evident is that when the spun sugar products described herein are added to water, the product disperses autogenously throughout the water and remains dispersed. In most instances, one observes a general cloudiness associated with a colloidal suspension. But this is not always the case. Several other novel phenomena have been observed also.

In U.S. Pat. No. 5,011,532, oleaginous substances, such as vegetable oil, mineral oil, baby oil, margarine, lanolin, cocoa butter and the like are disclosed as characteristically lacking affinity for water. The '532 patent explains how this characteristic is altered by mixing the oleaginous substance with sugar and melt-spinning the mixture in a cotton candy spinning machine or the equivalent. As so modified, the products disperse in water forming a colloidal or pseudo-colloidal dispersion. Such modification enabled such widely disparate procedures as: (a) incorporating shortening oil in a cake mix containing flour but no egg to which water is added to produce a batter; and (b) producing a confection or medicated lozenge by dehydrating the dispersion and allowing the melted residue to solidify. The disclosure of the '532 patent is incorporated herein by reference.

Other disclosures dealing with spinning substances with one or more sugars will be found in U.S. Pat. Nos. 4,873,085; 4,997,856; 5,028,632 and 5,034,421.

While significant advancements have been achieved for enhancing the dispersibility of oleaginous materials in liquids, artisans have long sought to improve the dispersibility of oleaginous materials in foods to enhance gustatory qualities. For example, meat alternatives such as meat by-products and edible protein compositions have enjoyed only limited success in spite of their lower costs. Consumers have, for the most part, shunned such products due to their lack of taste and dry texture. If these shortcomings could be overcome, more appealing food products would result.

It is, therefore, an object of the present invention to provide oleaginous materials in a format which would enhance edible compositions.

Other and further objects of the present invention will become apparent in the following description and its scope will be pointed out with the appended claims.

SUMMARY OF THE INVENTION

The present invention includes an oleaginous-containing matrix formed by melt-spinning an oleaginous substance with a carrier material. The oleaginous substances included therein are edible oils such as vegetable oils including soybean, corn, canola and the like. Alternatively, meat fats, hydrogenated vegetable oils, tallows, lards or fish oils are selected. The oleaginous substances make up from about 2 to about 40% by weight of the matrix, with amounts of from about 10 to about 30 being preferred and amounts of from about 15 to about 22% being most preferred.

The carrier materials included in the matrix are saccharides such as sucrose or maltodextrins and/or water-soluble cellulosic materials such as methyl or ethyl cellulose. In further aspects of the invention, the matrix includes one or more adjunct materials such as natural or artificial flavors, spices and/or hydrogels such as xanthan gum or alginates to enhance the matrix and/or products to which the matrix is included.

The oleaginous-containing matrix can be included with a variety of food products. For example, animal meats such as ground beef or hamburger, meat by-products, seafoods and proteinaceous products such as soy or vegetable-based meat alternatives.

The present invention further includes a process for preparing food products. An oleaginous matrix such as that described above is combined with a proteinaceous material to provide the product. The method described herein may be used to provide hamburger products, turkey or seafood-based products, soy-based or vegetable-based products in the form of patties, steaks, fillets or as part of other protein-containing food products.

As a result of the present invention, various edible protein compositions are provided which have enhanced taste and mouthfeel due to the inclusion of the oleaginous matrix. In one particularly interesting aspect, a portion of a meat product's fat content is replaced with a matrix containing a much lower amount of fat without a detectable loss of flavor or mouthfeel. In certain products, up to 50% of the usual fat content can be replaced without compromising gustatory qualities.

DETAILED DESCRIPTION OF THE INVENTION

The present invention concerns formation of an oleaginous-bearing matrix formed by melt-spinning oleaginous substances with carrier materials. The matrix is included in various food products.

The spinning process is preferably carried out with "cotton candy" fabricating-type equipment. The floss spinning machine used herein can be any cotton candy-type machine such as the Econofloss model 3017 manufactured by Gold Medal Products Company of Cincinnati, Ohio. It will be appreciated by those skilled in the art from the present description that any apparatus or physical process which provides similar forces and temperature gradient conditions can also be used. For simplicity in disclosing and describing this invention, the term "melt-spinning" will be understood to mean a flash-flow process which includes a combination of temperature, shear, flow, flow rate, mechanical forces and thermal gradients of the type used in a cotton candy-type machine. The apparatus is operated at a temperature and speed which permits flash flow but does not deteriorate the material undergoing the processing. Usually the resulting matrix product is in the form of a particle, flake, spicule, or other generally non-descript aggregate capable of subsequent processing in accordance with generally accepted techniques.

The melt-spinning process for producing the matrix includes melting a mixture containing the oleaginous material and carrier and forcing the ingredients through spinnerettes under conditions of high temperature and shear as disclosed above. The extremely short amount of time the ingredients are exposed to the melt-spinning temperature and shear allows the matrix to be formed without adverse effects.

The flash flow process contemplates subjecting carrier solids to a melt-spin process (or conditions comparable thereto) which provide sufficient internal flow to permit the transition in structure without degradation of the material. Internal flow occurs when the infrastructure of the material breaks down sufficiently to permit movement of material at a subparticle level, and probably at a molecular level. At a molecular level, internal flow contemplates the movement of molecules relative to each other.

Internal flow of material is generally associated with melting point or glass transition point. However, it is contemplated that the combined application of heat and external force is sufficient to produce the flow at temperatures below the melting or glass transition point for most compositions.

The oleaginous substance is present in amounts of from about 2 to about 40% by weight of the matrix. Amounts of from about 10 to about 30% by weight of the matrix are preferred, while amounts of from about 15 to about 22% are most preferred.

In one aspect of the present invention, the oleaginous substance is a food-acceptable/edible oil. Such substances are selected from vegetable oils, soybean oil, canola oil, corn oil, sunflower oil, olive oil, mixtures thereof and the like. In this aspect, the oils are preferably low in saturated fats.

In a further aspect, the matrix may be formed by including a fat such as an edible animal fat or fatty material. For example, beef, pork, lamb or similar animal fats or mixtures thereof may be used. Similarly, fat-containing materials such as beef tallow, sheep tallow, butter or lards, hydrogenated animal and/or vegetable oils may be included in the matrix. Moreover, fish or crustacean-based oils or oleaginous materials are also useful. Combinations of the above-described oleaginous materials are also contemplated.

The carriers included in the matrix are preferably saccharide-based and/or water-soluble cellulosic materials or mixtures thereof. A non-limiting list of suitable saccharide carriers include sucrose, lactose, fructose, dextrose, sorbitol, mannitol, maltose, synthetically-derived saccharide materials such as polydextrose, and the like and mixtures thereof. Alternative saccharide materials such as maltodextrins and/ or corn syrup solids are also useful. Suitable water-soluble cellulosic materials include methylcellulose, ethylcellulose, hydroxymethyl or ethylcellulose, alkali-metal salts of carboxymethylcelluloses and the like and mixtures thereof.

The oleaginous material and saccharide carrier matrix materials can also be processed with additional component(s). Such additional component(s) are primarily food related and do not detract from the appearance or utility of the matrix. The nature and amount of additional components used with the matrix materials will vary the properties of the final matrix such as by affecting taste, color, shape and/or size of the matrix.

Thus, in one aspect of the invention, ingestible food and/or food ingredient materials can be combined with the matrix materials prior to melt-spinning. For example, a broad range of natural and artificial flavor compositions and mixtures thereof are suitable. The flavors can be spices such as onion, garlic, salt, pepper and so forth. Also contemplated are natural and/or artificial meat flavors, smoke flavors and the like. Furthermore, ingredients such as food sauce materials, condiments, gravy mixes, nutritional supplements, low-calorie food materials, food conditioning agents, dehydrated vegetable and/or animal fluids, vitamins and/or minerals, preservatives, emulsifiers and the like and mixtures thereof may be added. In short, it is contemplated that any suitable food ingredient may be included in the matrix of the present invention. Those skilled in the art will realize that the above list is merely illustrative and not intended to exclude ingredients known to be within the scope of edible ingredients. The amount and combination of edible ingredients will depend upon the particular ingredients selected and the preference of the artisan.

In a further embodiment, the matrix may be formed by including a hydrogel with the matrix materials. Examples of suitable hydrogels include materials such as xanthan gum, guar gum, carrageenan gum, gum tragacanth, alginates such as sodium alginate, gum karaya, locust bean gum, gum acacia and mixtures thereof. The hydrogels function as binding agents and help to retain moisture in the food product. The hydrogel can be present in amounts of from about 0.2 to about 4% by weight of the matrix, with amounts of from about 0.8 to about 2.5% being preferred and amounts of from about 1.2 to about 2.2% by weight being most preferred.

The oleaginous matrix is especially well-suited for proteinaceous-based food products and preferably products containing at least 60% edible protein. Such products include meat products, fish, crustacean-based and/or protein-based compositions such as soy or vegetable products. The carrier portion of the matrix is rapidly soluble even when in contact with the minimal amount of moisture present in leaner cuts of meat. In this regard, the juices which are present in the meat and released during cooking dissolve the carrier, allowing the uniform colloidal distribution of the oleaginous materials and optionally present materials but having a distinct tendency to keep the oils in the product. The matrix will be present in the product in amounts of from about 0.5 to about 10% by weight of the final products, with amounts of from about 1 to about 7% being preferred, and amounts of from about 3 to about 6% being most preferred.

The oleaginous-containing matrix can be combined with a wide variety of meats such as beef, pork, lamb, chicken, turkey, horsemeat, and the like and mixtures thereof to provide a wide array of enhanced products. In addition, the matrix may be combined with protein materials such as soy or vegetable-based products. Examples of such products include soy, soy burger additives or vegetable by-products. It is contemplated that the inventive matrix can be combined with most food products to provide enhanced flavor including those products containing flours and starches.

In a further aspect of the invention, the spun matrix can be used to enhance the flavor and texture characteristics of seafoods and seafood-like products such as reconstituted or imitation fish products or crustacean products. Spun matrix compositions containing oils, such as fish oils, when added to inexpensive fish meat, such as pollack, provide taste characteristics associated with the more expensive grades of fish, i.e. such as crab legs. In addition, spun matrix products containing butter, butter flavors and spices can be efficiently incorporated in fish products to provide enhanced value products.

The oleaginous-based matrix can also be used to enhance the taste of meats as a colloidal dispersion. In this aspect of the invention, a sufficient quantity of the oleaginous matrix flakes, floss or spicules are dispersed in a liquid such as water and/or a meat broth to form a dispersion. The dispersion is then injected or otherwise introduced into meats to enhance its taste, texture and value. A non-limiting list of suitable meats included in this embodiment include poultry such as turkey, chicken or capon; pork such as hams or roasts; beef such as roast beef or steaks. The oleaginous dispersions are also useful for inclusion in ground and/or processed meats.

It is also contemplated that the matrix can be included in most processed meat products, especially those which normally include a substantial level of fat in order to obtain a desired taste characteristic. For example, hot dogs, sausages, bratwursts, beef jerky, pet foods and the like may be prepared to include the matrix.

It has been surprisingly found that exceptionally tasty meat products can be prepared by exchanging a portion of the fat typically present in a meat or protein-based product with a fat-containing matrix. In this aspect, the accustomed flavor and lubriciousness is achieved with a significantly reduced fat loading. For example, a typical beef hamburger product can be prepared by mixing or extruding ground beef and 20–30% fat. A spun matrix containing a mixture of 20% animal fat and 80% carrier can be combined with the ground beef and provides most of the same organoleptic qualities but with substantially less fat in the overall product.

An additional advantageous property of the present invention is the unexpected ability of the matrix to extend the shelf-life of the food products it is contained in. While applicant is not bound by theory, it appears that the use of spun matrix saccharides such as polydextrose, sucrose, maltodextrins, etc. have an antioxidant and bactericidal effect on edible proteins when incorporated therein. The extended shelf-like is apparent in ground chicken, ground turkey and ground beef. The effect is especially advantageous when the meat has low salt levels.

The carrier, oleaginous material and optionally present ancillary materials such as flavorant(s) or hydrogels can be combined to form a matrix in the following manner:

All ancillary materials, if included, are uniformly mixed; the oleaginous materials including any meat fat, tallow or the like is thereafter combined, preferably as a liquid with the ancillary materials mixture; the carrier is added to the above ingredients and thoroughly mixed; finally, the ingredients are spun in a melt-spinning-type machine such as that described herein to produce a matrix in the form of a floss, chip, spicule or the like depending on the particular ingredients included. The exact shape of the matrix is not considered a limiting aspect of the invention.

The matrix is then combined with protein-based materials such as meat or soy-based products or seafoods along with other and/or additional ancillary edible ingredients such as spices, preservatives, colorants, dyes and so forth, if desired. Finally, the food product can be cooked, packaged or stored. The matrix and protein-containing material are preferably combined prior to cooking in any manner which will assure that the matrix is sufficiently distributed throughout the product. Upon heating the novel edible products, the matrix releases the oleaginous material and any matrix-containing ingredients uniformly throughout the product. The release of the materials from the matrix also assures that the texture and moisture level characteristics achieved mimic those of the type the consumer is accustomed to.

The edible products containing the matrix can also include ancillary materials such as colorants, preservatives, dyes and the like. Such materials may be included in addition to or in lieu of those ancillary materials included in the matrix. Suitable auxiliary agents may be selected from any of the numerous food-acceptable materials known to those with ordinary skill in the art and may be included in amounts also known to the artisan. Any such auxiliary agents may either be melt-spun with the matrix ingredients or admixed with the protein material separately.

EXAMPLES

The following examples serve to provide further appreciation of the invention but are not meant in any way to restrict the effective scope of the invention.

EXAMPLE 1

SPUN MATRIX IN GROUND BEEF

| Ingredients | Weight % |
| --- | --- |
| Sucrose | 80 |
| Canola Oil | 20 |

In this example the spun matrix was prepared by uniformly mixing the sucrose with canola oil. The mixture was spun at 3600 r.p.m. at 200° C. to produce floss. The floss was mixed with ground beef in accordance with the following table. Beef hamburger compositions set forth in the following table were pressed in a 4-inch square hamburger press to form patties. The patties were fried on an electric skillet set at 350° F. for 3 minutes on each side, surface dried on a paper towel and analyzed. A three inch diameter center plug was pressed in a two-stage potato press to extract liquids to determine liquid or juiciness content.

| Hamburger Sample | Prefried Weight (grams) | Pressed weight of Fried 3-inch Diameter (grams) | Weight of Liquids from Fried 3-inch Diameter (grams) | Ratio of Liquids to Solids (%) |
| --- | --- | --- | --- | --- |
| Hamburger With 20% Beef Fat | 144 | 65.0 | 24.8 | 38.2 |
| Water | 6 | | | |
| Hamburger With 10% | 144 | 63.5 | 26.0 | 40.9 |

| Hamburger Sample | Prefried Weight (grams) | Pressed weight of Fried 3-inch Diameter (grams) | Weight of Liquids from Fried 3-inch Diameter (grams) | Ratio of Liquids to Solids (%) |
| --- | --- | --- | --- | --- |
| Beef Fat | | | | |
| Water | 6 | | | |
| Hamburger with 10% | 132 | 56.7 | 26.9 | 47.4 |
| Beef Fat | | | | |
| Water | 6 | | | |
| Floss | 12 | | | |
| Hamburger With 10% | 138 | 60.8 | 26.9 | 44.2 |
| Beef Fat | | | | |
| Water | 6 | | | |
| Floss | 6 | | | |

The samples containing floss and corresponding reduced amount of hamburger had higher weights of juice. Also, the ratio of liquids to solids in such samples is higher than hamburger with 20% beef fat. The hamburgers containing floss were thicker after frying than the fried hamburgers without floss. The appearance, texture and mouthfeel of the low fat hamburgers prepared with the floss were judged to be better than the control low fat hamburger and virtually identical to that of the high fat hamburgers.

EXAMPLE 2

SPUN MATRIX IN GROUND BEEF

| Ingredients | Weight % |
| --- | --- |
| Polydextrose | 80 |
| Canola Oil | 20 |

In this example, the spun matrix was prepared by uniformly mixing the polydextrose with canola oil. The mixture was spun at 3600 r.p.m. at 140° C. to produce large dry flakes. The flakes were mixed with ground beef in accordance with the following table. Beef hamburger compositions set forth in the following table were pressed in a 4-inch square hamburger press to form patties. The patties were fried on an electric skillet set at 350° F. for three minutes on each side, surface dried on a paper towel and analyzed. A three inch diameter center plug was pressed in a two-stage potato press to extract liquids to determine liquid or juiciness content.

| Hamburger Sample | Prefried Weight (grams) | Pressed Weight of Fried 3-inch Diameter (grams) | Weight of Liquids from Fried 3-inch Diameter (grams) | Ratio of Liquids to Solids (%) |
| --- | --- | --- | --- | --- |
| Hamburger With 20% | 144 | 65.0 | 24.8 | 38.2 |
| Beef Fat | | | | |
| Water | 6 | | | |
| Hamburger With 10% | 144 | 63.5 | 26.0 | 40.9 |
| Beef Fat | | | | |
| Water | 6 | | | |
| Hamburger with 10% | 132 | 53.3 | 26.5 | 49.7 |
| Beef Fat | | | | |
| Water | 6 | | | |
| Flakes | 12 | | | |
| Hamburger With 10% | 138 | 58.6 | 26.8 | 45.7 |
| Beef Fat | | | | |
| Water | 6 | | | |
| Flakes | 6 | | | |

The samples containing flakes and corresponding reduced amount of hamburger had higher weights of juice. Also, the ratio of liquids to solids in both matrix-containing samples was higher than even the hamburger containing 20% beef fat. The hamburgers containing flakes were also thicker after frying than the fried hamburgers without flakes. The appearance, texture and mouthfeel of the low fat hamburgers prepared with flakes was better than either of the non-floss containing hamburgers.

EXAMPLE 3

SPUN MATRIX IN SOY BURGERS

| Ingredients | Weight % |
| --- | --- |
| A. Floss | |
| Sucrose | 80 |
| Canola Oil | 20 |
| B. Flakes | |
| Polydextrose | 80 |
| Canola Oil | 20 |

In this example, the spun matrices were prepared by uniformly mixing the sucrose with canola oil for the floss matrix A and polydextrose with canola oil for the flake matrix B. The A mixture was spun at 3600 r.p.m. at 200° C. to produce floss, and the B mixture was spun 3600 r.p.m. at 140° C. to produce flakes. The floss and flakes were separately mixed with soyburger available from Organic Processing Corporation of Xenia, Ohio in accordance with the following table. Soyburger compositions set forth in the following table were pressed in a 4-inch square hamburger press to form patties. The patties were fried in an electric skillet set at 350° F. for four minutes on each side, and analyzed. The burger was pressed in a two-stage potato press to extract liquids to determine liquid or juiciness content.

| Sample | Prefried Weight (grams) | Pressed Weight of Fried Sample (grams) | Weight of Liquids From Fried Sample (grams) | Ratio of Liquids to Solids (%) |
|---|---|---|---|---|
| Soyburger | 150 | 122.09 | 7.5 | 6.0 |
| Soyburger | 138 | 99.69 | 17.5 | 17.6 |
| Sucrose Floss | 12 | | | |
| Soyburger | 138 | 110.69 | 12.0 | 10.8 |
| Polydextrose Flakes | 12 | | | |

The samples containing floss or flakes and corresponding reduced amount of soyburger had higher weights of juice. Also, the ratio of liquids to solids in the inventive samples is higher than soyburger control. The juices which were extracted from the floss or flake containing soyburgers was a pleasant tasting oily liquid whereas the little juice obtained from the control was waterlike and had a bitter taste.

EXAMPLE 4

SPUN MATRIX IN GROUND TURKEY

| | Ingredients in Flake | Weight % |
|---|---|---|
| A. | Floss | |
| | Sucrose | 80 |
| | Canola Oil | 20 |
| B. | Polydextrose Flakes | |
| | Polydextrose | 80 |
| | Canola Oil | 20 |
| C. | Maltodextrin Flakes | |
| | Maltodextrin (Hubinger-Dri-Sweet) | 80 |
| | Canola oil | 20 |

In this example the spun matrix was prepared by uniformly mixing: (a) the sucrose and canola oil for Part A; (b) the polydextrose with canola oil for Part B; and (c) the maltodextrin with canola oil for Part C. Each of the B and C mixtures, were spun at 3600 r.p.m. at 140° C. and produced large dry flakes. The A mixture was spun at 3600 r.p.m. and 200° C. to produce floss. Each of the flakes and floss were individually mixed with ground turkey (93% lean) in accordance with the following table.

Turkeyburger compositions set forth in the following table were pressed in a 4-inch square hamburger press to form patties. The patties were fried in an electric skillet at 350° F. for six minutes on each side and analyzed. The samples were pressed in a two-stage potato press to extract liquids to determine liquid or juiciness content.

| Sample | Prefried Weight (grams) | Pressed Weight of Fried Sample (grams) | Weight of Liquids from Fried Sample (grams) | Ratio of Liquids to Solids (%) |
|---|---|---|---|---|
| Turkeyburger with 7% Fat | 150 | 88.8 | 23.9 | 26.9 |
| Turkeyburger with 7% Fat | 144 | 89.8 | 28.5 | 31.7 |
| Polydextrose Flakes | 6 | | | |
| Turkeyburger with 7% Fat | 126 | 82.7 | 25.6 | 31.0 |
| Water | 12 | | | |
| Floss | 12 | | | |
| Turkeyburger with 7% Fat | 144 | 88.0 | 33.0 | 37.5 |
| Maltodextrose Flakes | 6 | | | |

The samples containing flakes and floss and corresponding reduced amount of hamburger had higher weights of juice. Also, a ratio of liquids to solids in such samples is higher than the turkeyburger control. The turkeyburgers containing flakes were thicker after frying than the fried turkeyburgers without flakes. Finally, the appearance, texture and mouthfeel of the turkeyburgers with the flakes was much better than the control. The turkey burgers with flakes had a smooth firm texture and the control had a dry, coarse, granular texture.

The burgers with flakes had approximately the same pressed weight as the control even though less turkeyburger was used to make the patty. It appears that the addition of water to the patty mixture is not necessary with turkeyburger since better results are obtained when the flakes and floss are added directly to the turkeyburger composition without additional water.

The example was repeated using beef flavored canola oil obtained from Bunge Foods and was used in place of the oil in matrix C. The canola/maltodextrin mixture was spun at 3600 r.p.m. at 140° C. The turkeyburger prepared with this matrix exhibited enhanced juiciness over the control and a beef flavor was present.

EXAMPLE 5

PROTEIN PRODUCT ENHANCEMENT MATRIX

| Ingredient | Weight % |
| --- | --- |
| Maltodextrin D.E. 36 | 50–92 |
| Oleaginous Component | 8–36 |

In this example, the saturated fat component of a protein product has been significantly reduced by the use of a maltodextrin-based spun matrix. The matrix is formed by combining a low amount of oleaginous material, such as animal fat, or replacement such as canola oil, etc., at a percentage such that it is significantly reduced when compared to the oleaginous content of a fat-bearing protein product. The material is processed by subjecting it to flash flow conditions such as that described herein to form a flake-like particulate material. The matrix is recovered from the process and can then be introduced into a protein product such as hamburger, a soy patty, seafood or other protein material. The recovered particulate admixes more efficiently with meat and other protein media than does the oleaginous material alone.

The result is a significantly reduced saturated fat product which emulates the texture mouthfeel and taste of a high fat content protein product. As a result of this unique combination, meat and protein-based products can be processed to significantly reduce the fat content yet to preserve the organoleptic qualities.

EXAMPLE 6

HAMBURGER FLAVORANT MATRIX

| Ingredients | Weight % |
| --- | --- |
| Maltodextrin D.E. 36 | 78.0 |
| Canola Oil | 20.0 |
| Spices- | |
| including salt, beef flavor, pepper, garlic and onion | 2.0 |
| | 100.0 |

In this example, a flavorant-containing matrix was prepared which is suitable for enhancing the flavor of hamburger. First, the spices were uniformly mixed and thereafter combined with the oil. The maltodextrins were added to the oil-spice mixture until a uniform mixture was obtained. The uniform mixture was processed at a low setting yielding a spicy, beef-flavored flake.

While the best overall taste, texture and mouthfeel is obtained when the flakes or floss are used in fresh meat, the largest relative difference between the control and ground meat containing flakes or floss has been observed in frozen ground meats. In particular, the flakes or floss are added to ground meat held at substantially the freezing point, e.g. below 5° C. and then the mixture is promptly frozen and preferably flash frozen to lower than 5° C. When the frozen patties prepared in this manner are flame broiled, fried or microwaved, the patties containing floss or flakes of type used in Examples 1–6, have more retained liquids as compared to pressed solids and have improved taste, texture and mouthfeel.

In those embodiments where water is added to the above mixture to make frozen patties, it is preferably added as shaved or finely crushed ice.

While there have been described what are presently believed to be the preferred embodiments of the invention, those skilled in the art will realize that changes and modifications may be made thereto without departing from the spirit of the invention, and it is intended to claim all such changes and modifications as fall within the true scope of the invention.

What is claimed is:

1. A method of preparing a food product, comprising mixing a matrix, formed by melt-spinning a mixture of an oleaginous substance and a saccharide carrier to provide internal flow thereby permitting transition in structure with degradation of said oleaginous substance and saccharide carrier with a ground meat material maintained at a temperature of above freezing but below 5° C. to form a mixed composition and then promptly freezing such mixed composition.

2. The method according to claim 1, wherein the mixed composition is flash frozen to a temperature lower than −5° C.

3. The method according to claim 1 wherein shaved or crushed ice is added to the composition prior to freezing the composition.

4. The product made by the process of claim 1.

* * * * *